(12) United States Patent
Shoham et al.

(10) Patent No.: US 9,510,959 B2
(45) Date of Patent: Dec. 6, 2016

(54) STENT FOR RESTENOSIS PREVENTION

(75) Inventors: Moshe Shoham, Hamovil (IL); Amit Reches, Binyamina (IL); Lucy Leshansky, Haifa (IL); Michael Groskop, Tel-Aviv (IL); Shachar Millis, Pardess Hanna-Karkur (IL); Yishai Pentanovich, Pardess Hanna-Karkur (IL)

(73) Assignee: Technion Research & Development Foundation Ltd., Haifa (IL)

( * ) Notice: Subject to any disclaimer, the term of this patent is extended or adjusted under 35 U.S.C. 154(b) by 0 days.

(21) Appl. No.: 14/008,556

(22) PCT Filed: Mar. 28, 2012

(86) PCT No.: PCT/IL2012/000133
§ 371 (c)(1),
(2), (4) Date: Mar. 3, 2014

(87) PCT Pub. No.: WO2012/131671
PCT Pub. Date: Oct. 4, 2012

(65) Prior Publication Data
US 2014/0180392 A1    Jun. 26, 2014

Related U.S. Application Data

(60) Provisional application No. 61/457,439, filed on Mar. 28, 2011.

(51) Int. Cl.
*A61F 2/852* (2013.01)
*A61F 2/91* (2013.01)
(Continued)

(52) U.S. Cl.
CPC .............. *A61F 2/852* (2013.01); *A61F 2/91* (2013.01); *A61B 2017/00411* (2013.01);
(Continued)

(58) Field of Classification Search
CPC .......... A61F 2002/30064; A61F 2/06; A61F 2/852; A61F 2/07; A61F 2002/30079; A61L 31/16
USPC ................................................ 623/1.21, 1.44
See application file for complete search history.

(56) References Cited

U.S. PATENT DOCUMENTS

| 6,015,387 A * | 1/2000 | Schwartz ............. A61B 5/0031 600/12 |
| 6,092,530 A * | 7/2000 | Weissman ............ A61B 5/0031 128/899 |

(Continued)

OTHER PUBLICATIONS

Extended European Supplementary Search Report of the European Patent Office, in corresponding European patent application No. 12763630.6, dated Aug. 18, 2014.
(Continued)

*Primary Examiner* — Christian Sevilla
*Assistant Examiner* — Seema Mathew
(74) *Attorney, Agent, or Firm* — Daniel Feigelson; Fourth Dimension IP

(57) ABSTRACT

A device for use in reducing or preventing the occurrence of restenosis following procedures such as PTCA, in which a stent is used to hold a bodily lumen open. The device comprises a two layered stent, one lying within the other. Both stent layers have an open weave structure, such that they can expand to the correct dimensions after implantation. The outer stent layer is static and grips the inner wall of the lumen in which it is deployed in the usual manner. The inner layer stent is constructed such that it can be vibrated relative to the outer static stent layer. The inner layer stent may be made of a material which can be vibrated from an external source, such as a ferromagnetic material. This vibration prevents restenosis of the treated lumen. Alternatively, a vibrator, such as a piezoelectric device, can be installed on the inner stent layer.

7 Claims, 3 Drawing Sheets

(51) Int. Cl.
    *A61F 2/30*     (2006.01)
    *A61F 2/06*     (2013.01)
    *A61F 2/07*     (2013.01)
    *A61B 17/00*     (2006.01)

(52) U.S. Cl.
    CPC . *A61F 2/06* (2013.01); *A61F 2/07* (2013.01); *A61F 2002/30079* (2013.01); *A61F 2210/009* (2013.01); *A61F 2210/0076* (2013.01); *A61F 2230/0054* (2013.01)

(56) References Cited

U.S. PATENT DOCUMENTS

| | | |
|---|---|---|
| 6,165,209 A | 12/2000 | Patterson |
| 6,296,619 B1 | 10/2001 | Brisken |
| 6,416,540 B1 | 7/2002 | Mathur |
| 6,849,069 B1 | 2/2005 | Clayman |
| 7,857,766 B2 | 12/2010 | Lasater |
| 2005/0209682 A1 | 9/2005 | Abraham-Fuchs |
| 2006/0129216 A1* | 6/2006 | Hastings .............. A61B 5/0215 607/115 |
| 2007/0168016 A1 | 7/2007 | Gronemeyer |
| 2008/0033527 A1* | 2/2008 | Nunez ................. A61B 5/0215 623/1.13 |
| 2008/0058633 A1* | 3/2008 | Boyden .............. A61B 5/02007 600/407 |
| 2008/0119421 A1* | 5/2008 | Tuszynski ........... A61K 31/195 514/34 |
| 2009/0036975 A1* | 2/2009 | Ward .................. A61B 5/0031 623/1.18 |
| 2009/0295383 A1 | 12/2009 | Gianchandani |
| 2010/0318173 A1 | 12/2010 | Kolandaivelu |
| 2014/0180397 A1* | 6/2014 | Gerberding ............. A61F 2/852 623/1.16 |
| 2014/0214149 A1* | 7/2014 | Kuraguntla ............... A61F 2/07 623/1.15 |

OTHER PUBLICATIONS

PCT/IL2012/000133 International Search Report and Written Opinion of the International Searching Authority, dated Sep. 14, 2012.

\* cited by examiner

STENT FOR RESTENOSIS PREVENTION

This is a national phase application of PCT/IL2012/000133, entitled "STENT FOR RESTENOSIS PREVENTION", which was filed on Mar. 28, 2012 and claims the priority of and benefit of U.S. provisional application No. 61/457,439, also entitled "STENT FOR RESTENOSIS PREVENTION", which was filed on Mar. 28, 2011. The contents of said applications are incorporated herein by reference.

FIELD OF THE INVENTION

The present invention relates to the field of stents for medical applications, especially for use in the prevention of restenosis.

BACKGROUND OF THE INVENTION

Stents are used in medical practice to provide support to various lumens in the human body. One of the most common uses is in conjunction with percutaneous transluminal coronary angioplasty (PTCA), which is used to treat stenosis, a narrowing of a blood vessel, leading to restricted blood flow. In PCTA, a balloon inserted into the narrowed section of the artery 'squashes' the cholesterol plaques (atherosclerosis) against the artery walls, thus widening the size of the lumen and increasing blood flow. A stent is often used in conjunction with angioplasty to hold open an artery, allowing for unrestricted blood flow, or to support a weakness in the artery wall called an aneurysm. The artery can react to the stent, perceive it as a foreign body and respond by mounting an immune system response which leads to renewed narrowing near to or inside the stent. Such a reoccurrence of stenosis is known as Restenosis.

Furthermore, the action of the angioplasty itself can cause damage to the artery walls, and it responds by using physiological mechanisms to repair the damage. Damage to the blood vessel wall by angioplasty triggers physiological response that can be divided into two stages. The first stage, which may occur immediately after tissue trauma, is thrombosis. A blood clot may form at the site of the damage and further hinder blood flow. This is accompanied by an inflammatory immune response. The second stage may occur 3-6 months after surgery and is the result of proliferation of cells in the intima, a smooth muscle wall in the vessel. This is known as Neointimal hyperplasia (NIHA), and may occur in 20-30% of patients treated with bare metal stents.

Drug-eluting stents are stents coated with pharmaceuticals that inhibit tissue growth. By controlled release of the drugs onto the endothelial surface, the restenosis process may be controlled or inhibited, thus reducing the risk of restenosis from scar-tissue and cell proliferation. With such drug-eluting stents, the restenosis rate may be lowered to 5-10%, depending on the size and length of the diseased segments. They therefore reduce the need for a repeated procedure. However, compared with bare metal stents, there may be an increase in the thrombosis rate.

There therefore exists a need for a device for reducing restenosis following PCTA, or any other lumen support procedure using stents, and which overcomes at least some of the disadvantages of prior art systems and methods.

The disclosures of each of the publications mentioned in this section and in other sections of the specification, are hereby incorporated by reference, each in its entirety.

SUMMARY OF THE INVENTION

The present disclosure describes new exemplary devices for use in reducing or even preventing the occurrence of restenosis following procedures such as PTCA, in which a bodily lumen is held clear by means of a stent. The device provides a mechanical solution to the problem of restenosis, and is not dependent on the use of drugs, which can have undesired side effects. The device comprises a two layered stent, one layer lying within the other, and has the advantage that it can be installed by means of the same PTCA procedure as is used for any conventional prior art stent. Both stent layers have an open weave structure, such that they can expand to the correct dimensions after implantation. The outer stent layer is static and grips the inner wall of the artery in which it is deployed in the usual manner. The inner layer stent, on the other hand, is constructed such that it can be vibrated relative to the outer static stent layer. One exemplary way in which this can be achieved is to manufacture the inner layer stent of a material which, after installation of the double layered stent, can be vibrated from an external source relative to the static outer layer. Periodic vibration of this inner stent layer will dislodge any tissue growth formed within the double layered stent, thereby preventing its growth, and restenosis of the treated artery. Since the stent does not have to be drug eluting in order to perform its function, the potential problems of such drug eluting stents, namely increased danger of thrombosis, is absent.

Vibration of the inner layer of the stent can be performed by any long-range field interaction with an external driver. One method is to construct the inner stent layer of a ferromagnetic material, and to apply an alternating magnetic field from outside of the subject's body. The outer stent layer then has to be constructed of a non-ferromagnetic material to avoid shielding the inner vibrating stent layer from the activating magnetic field. The applied magnetic field could be adapted to have an alternating field direction such that the inner stent layer performs longitudinal vibrations or rotational vibrations or even stepped rotational movement. Any such movement regime will ensure that scar tissue growing through the openings of the outer stent layer will be cut or at least sufficiently damaged to prevent it from growing through the inner stent openings. The vibration procedure does not need to be performed continuously but can be performed at periodic intervals, according to the rate of growth of the ingrowing tissue. A mechanism is necessary to ensure that the inner sheath remains constrained within the outer sheath, so that it does not break free and pass down the artery which it is treating.

An alternative method is to construct the inner stent layer of a magnetic material, and to magnetize it so that the interaction with an applied alternating magnetic field is stronger and easier to control. Thus for instance, magnetizing the inner stent layer so that its poles are diametrically oppositely disposed, will enable rotational vibration is to be readily achieved by applying a simple alternating magnetic field normal to the direction of the blood vessel. Longitudinal vibration could be generated by magnetizing the inner stent layer such that it has poles disposed at opposite ends of the inner stent layer. In such a case the alternating magnetic field must be applied such that it has a varying amplitude parallel to the direction of the blood vessel in which the stent is deployed. As an alternative to constructing the inner stent layer of a magnetic material, it is feasible to attach tiny magnetic chips to the inner stent layer. Modern rare earth magnets having a high energy density could be feasible for this purpose.

Other methods of generating the vibrational motion of the inner stent layer is by the use of concentrated ultrasound energy, which can induce mechanical vibrations into any non-fixed element onto which the ultrasound energy is directed, such as the inner sheath.

Besides the implementation of vibrations by an externally applied activating field operating on a suitably receptive vibrating element on the internal stent sheath, or the internal stent sheath itself, it may also be possible to provide an on-board vibrating mechanism that will operate without external involvement. This would have the advantage of being able to operate in the background without user or medical staff intervention. One possible method is to use a micro-miniature vibrating motor, especially a vibrator of the piezoelectric type which is more energy efficient than a rotary motor, powered by an on-board battery. However, because of the difficulty of access to the device to change its battery when depleted, the battery should be chargeable. Such batteries can be charged by induction from an externally applied charging field, which would only be necessary at infrequent intervals. Alternatively, the battery could be maintained in a charged condition by utilizing energy from the subject's body itself. In the latter case, there are many methods and devices designed to internally harvest energy from the human body. Such energy could be in the form of heat, fluid flow, chemical, mechanical and electrical energy. One particularly convenient source of energy could be the pulsating behavior of the fluid flow within the lumen, especially arising from blood flow pulsations. Such pulsating flow could be used to operate electromechanical generators, such as based on MEMS devices, and the electrical energy produced in the generator could be used to charge the on-board battery. Another implementation could be to forego the need for an on-board battery, and to use the generated electrical energy to vibrate the device directly. All such cycles would thus convert the mechanical energy of the pulsating fluid, to electrical energy and then back to mechanical energy to vibrate the device. Further implementations could utilize the pulsating flow to generate the mechanical displacements themselves between the parts of the device, thus involving a mechanical to mechanical energy cycle.

Since the double layered stent must be capable of being deployed in the conventional manner, and not to restrict blood flow through it, whatever mechanism is used to generate the vibrations or motion must be such that it does not interfere with the stent deployment procedure nor with the blood flow. Consequently, any vibrational mechanisms installed on the stent itself, must be suitably miniaturized to prevent such interference. Both current and future nano-technological developments should make such applications implementable without interference in the flow maintaining function of the stent.

The current most common medical use of stents is probably for maintaining free flow through coronary blood vessels, and for supporting them. That is the application which has been generally used to describe the stent assembly invention in this disclosure. However, use of the stent assemblies described in this application is not intended to be limited to such blood vessels, and such stent assemblies can be used in other suitable bodily lumens, including bifurcated stents for use at lumen junctions. Some such applications include esophageal stents, duodenal stents, colonic stents, biliary stents, pancreatic stents, urinary tract and prostatic stents, and peripheral blood vessel stents.

It is thus to be understood that the stent assemblies described and claimed in this disclosure are intended for use in treating any suitable bodily lumen, whether specifically so described in this disclosure or not.

There is therefore provided, an exemplary stent assembly adapted for deploying within a bodily lumen, the stent assembly comprising:
(i) an outer element comprising a first expandable mesh sheath,
(ii) an inner element comprising a second expandable mesh, the inner element having a smaller expanded diameter to the outer element, and being disposed axially within the outer element, and in close juxtaposition thereto, and
(iii) a vibrating mechanism adapted to impart vibratory motion to the inner element.

In such a stent assembly, the inner element may comprise a material which can undergo vibrational motion under the influence of an externally applied effect. The material of the inner element may be a ferromagnetic material, or a magnetized material, or there may be at least one permanent magnet attached to the second sheath, and in all of these cases, the externally applied effect should be an alternating magnetic field.

Alternatively, the applied effect may be a directed ultrasound field, adapted to cause the inner element to vibrate when applied in the direction of the stent assembly.

Furthermore, in any of these above described stent assemblies, the externally applied effect may be applied in such a direction that the inner element vibrates longitudinally within the outer element, or rotationally within the outer element, or in such a direction that the inner element can rotate within the outer element.

As an alternative to the vibrating mechanism using an externally applied field, it may be disposed on the inner element. In such a case, the vibrating mechanism may comprise a piezoelectric vibrating motor, and it may also have a battery for activating the piezoelectric vibrating motor. The battery may advantageously be a rechargeable battery, which may be adapted to be recharged by use of an external inductive charging field. Alternatively, the stent assembly may further comprise a generator activated by flow of fluid through the lumen, and wherein the battery is adapted to be recharged by the generator.

In an even further implementation, the vibrating mechanism may comprise a mechanical converter for converting mechanical energy of flow of fluid in the lumen to vibrational energy applied to the inner element.

In any of the above described exemplary stent assemblies, at least one of the elements should comprise a tab to prevent the inner element from becoming freed from its location within the outer element.

Additionally, the bodily lumen in which the stent assembly is adapted to be installed, may be a blood vessel. The bodily lumen may include a junction in which the stent assembly is installed.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1A:
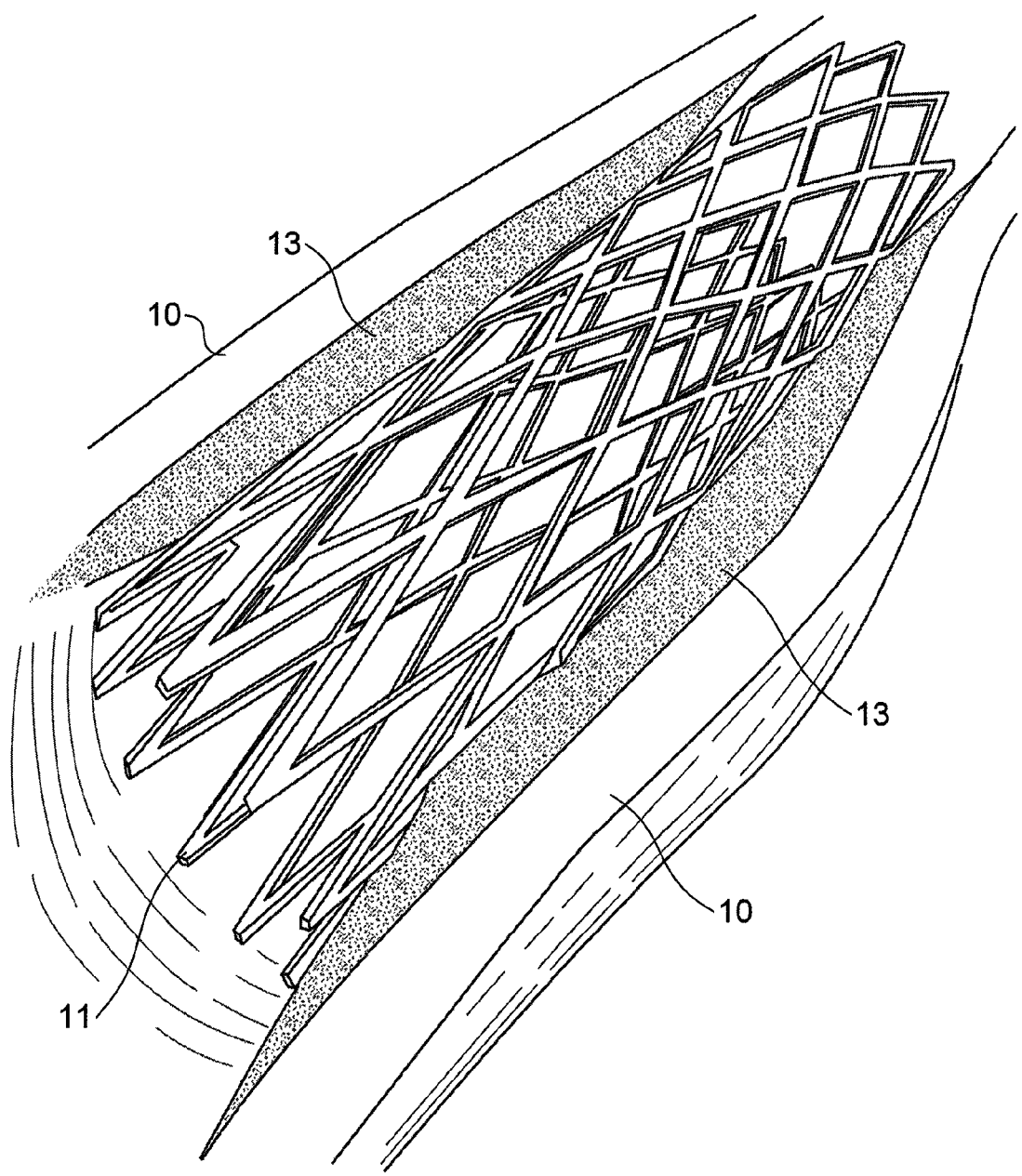
FIGS. 1A and 1B illustrate schematically a conventional prior art stent in its expanded state installed in a subject's artery.
Figure 1B:
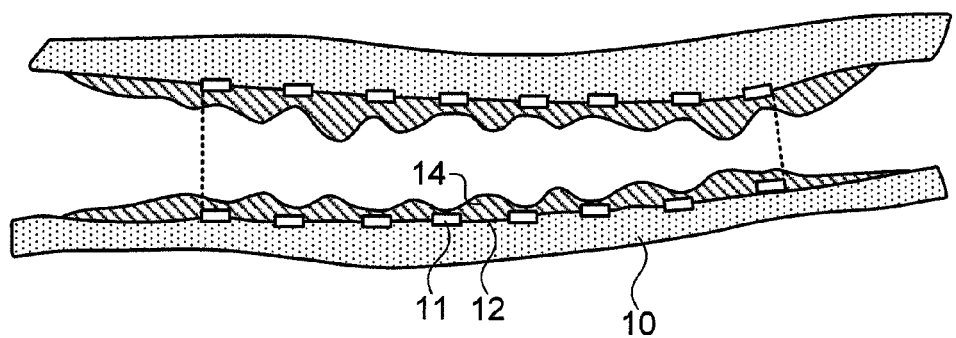

Reference is now made to FIGS. 1A and 1B, which illustrate schematically a cut-away view of a subject's artery 10 with a conventional prior art stent 11 in its expanded state installed therein. In FIG. 1A the stent 11 is shown, for illustrative purposes, in position on top of a layer of plaque 13 on the inner wall of a section of the artery 10, partially expanded and ready for the plaque to be compressed by means of the balloon inflation. The balloon and its inflation tubing and the guidewire are not shown in FIG. 1A, to increase clarity.

Reference is now made to FIG. 1B, which is a cross-sectional schematic view of the prior art stent 11 of FIG. 1A after installation in an artery 10. The wire mesh sections 11 of the stent are shown, slightly embedded into the wall of the artery, with spaces 12 between the wire mesh. To simplify the schematic drawing of FIG. 1B, the compressed plaque layer is not shown separately from the artery wall 10. The stent shown may be made of a stainless steel wire mesh, though other materials such as nitinol may be used, and fabric is even used for large arteries. In FIG. 1B, there is shown the effect of restenosis, in which excess scar tissue and neointimal tissue proliferation 14 has occurred through the openings 12 in the stent mesh 11, and has even spread to partially cover the mesh wires on the artery wall. Although in the drawing, the excess tissue growth 14 is marked distinctly from the artery wall tissue 10, it is to be understood that the tissue layers are contiguous, and that the sharp boundary line between them shown in FIG. 1B is only for graphic delineation purposes. This process has thus generated restenosis in the treated artery, which reduces the blood flow therethrough, and if the excess tissue growth continues, the subject will require angioplasty treatment again.

Figure 2:
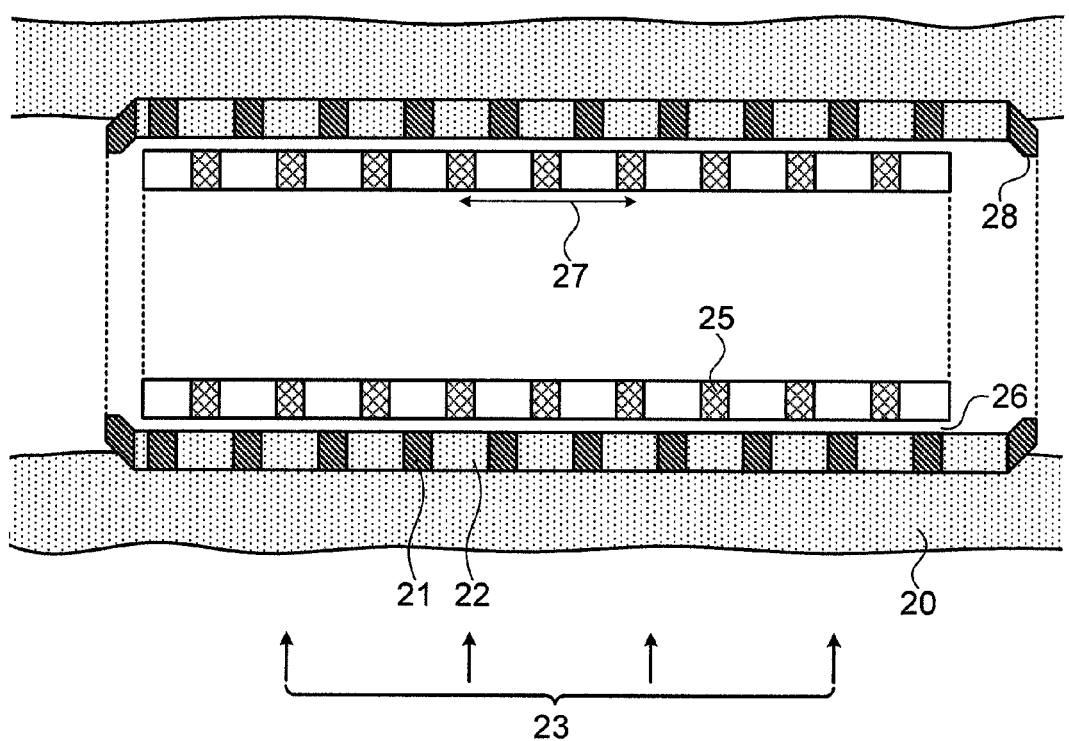
FIG. 2 is a schematic illustration of a novel stent, constructed according to the present disclosure.

Reference is now made to FIG. 2, which is an enlarged schematic illustration of a novel stent assembly constructed according to the present disclosure, and installed into the artery 20 of a subject. The stent assembly has two concentric wire mesh sheaths, both of which have been expanded by application of balloon pressure through their internal bores. FIG. 2 illustrates this stent assembly after having been installed for a period of time. The outer sheath 21 is seen to have been embedded in the artery wall, initially by the outward pressure of the balloon angioplasty, but then maintained in this position by the growth of tissue 22 from the artery wall into the spaces in the mesh of the outer stent sheath. The inner stent sheath 25 is shown in close contact with the outer stent sheath, but is free to move relative to the outer stent sheath 21. This freedom of movement is illustrated in FIG. 2 by the small space 26 shown between the sheaths, though this is merely a schematic rendering and is not meant to indicate the extent of the fit between the two sheaths. An externally applied force field 23 can cause the inner stent sheath to move or vibrate. This motion or vibration, executed at periodic intervals, has prevented the tissue growth from extending beyond the interface region 26 between the inner and the outer stent sheaths. The motion or vibration can be achieved either longitudinally, as shown by the arrow 27 in the drawing, or in rotation, which in FIG. 2 would mean rotation around an axis along the stent center line in the plane of the drawing, depending on the nature of the field applied. Tabs 28, or any other restraining element, may be provided on the outer sheath to constrain the inner stent sheath within the outer stent sheath, preventing the loose inner stent sheath from "escaping" into the artery in which the stent assembly has been implanted. Although in the implementation of FIG. 2, the restraining element is shown on the outer stent sheath, it is to be understood that it could equally well be fitted on the inner stent sheath, such as one or more tabs engaged with spaces in the outer stent sheath.

The inner stent sheath 25 could be made of a ferromagnetic material, and the applied force field 23 could be an alternating magnetic field applied from a coil or coils disposed outside the body of the subject. The inner stent sheath could even be made of a magnetic material, and be magnetized in order to provide stronger forces in the applied magnetic field. Application of this external force 23 and consequent motion 27 of the inner stent sheath prevents growth of the tissue from the outer stent sheath into the spaces of the inner stent sheath, preventing restenosis, and thus maintaining a clear passage in the artery.

For implementations in which the stent vibration is achieved by means of an integral vibrator (not shown in FIG. 2), this, together with its activating circuits and battery, if any, could be installed conformally on the mesh of the inner stent sheath, so as not to impede the flow of body fluids through the installed stent.

Figure 3A:
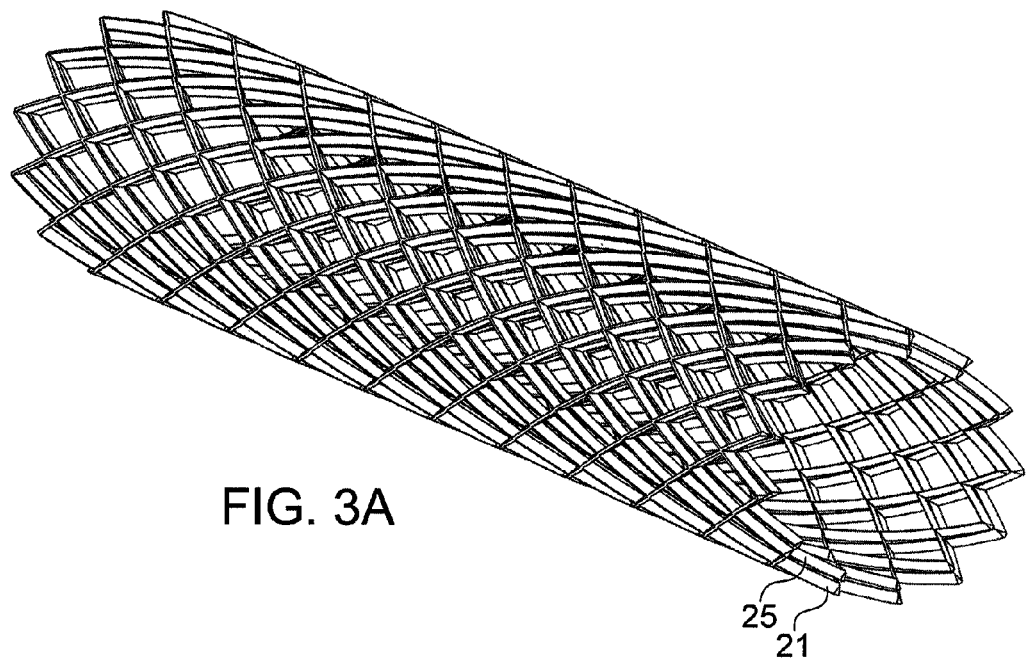
FIGS. 3A and 3B show different isometric views of the stent shown schematically in FIG. 2.
Figure 3B:
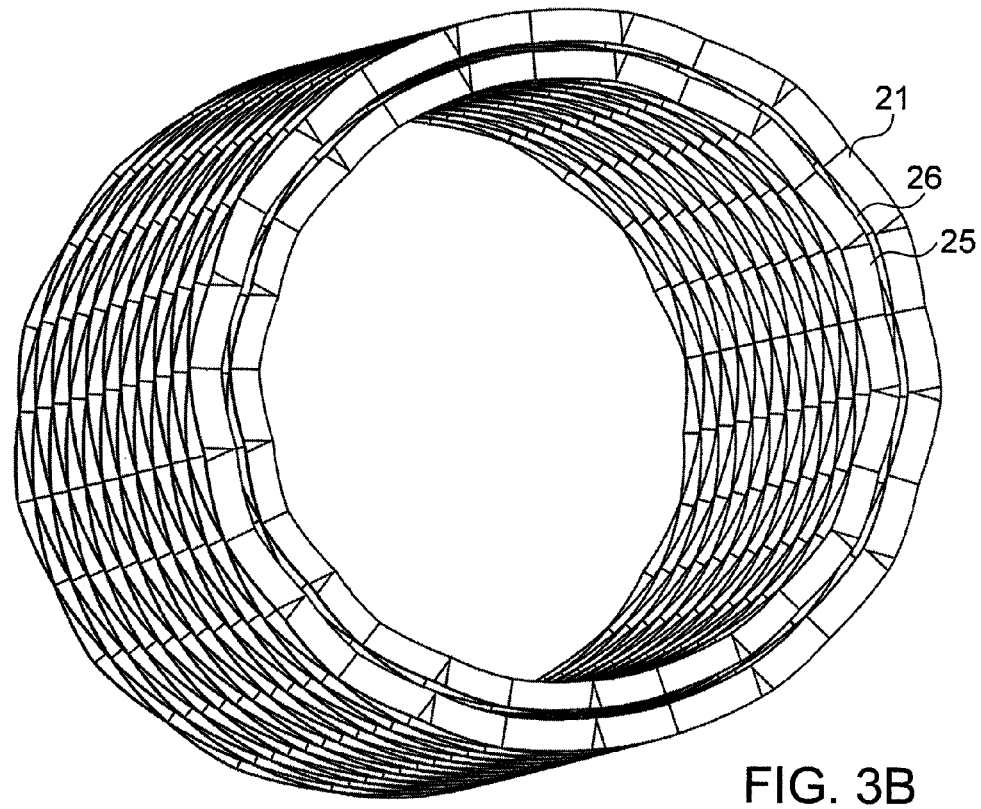

Reference is now made to FIGS. 3A and 3B, which show different isometric views of one implementation of the stent assembly shown schematically in FIG. 2. The exemplary implementation shown in FIGS. 3A and 3B uses stent sheaths with a diamond shaped mesh construction. FIG. 3A shows a side view of the stent assembly, while FIG. 3B shows an end view of the stent assembly, so that the inner vibrating stent sheath 25, the outer stent sheath 21 and the space 26 between them can be clearly seen.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A stent assembly for deploying within a bodily lumen, comprising:
    an outer element comprising a first expandable mesh sheath;
    an inner element comprising a second expandable mesh sheath, said inner element having a smaller expanded diameter than that of said outer element, and being disposed axially within said outer element, and in close juxtaposition thereto; and
    an integral vibrator mounted on said inner element and adapted to impart vibratory motion to said inner element without involvement external to said lumen, a converter system configured to convert the mechanical energy of flow of fluid in said lumen to vibrational energy.

2. A stent assembly according to claim 1 wherein at least one of said elements comprises a tab to prevent said inner element from becoming freed from its location within said outer element.

3. A stent assembly according to claim 1, wherein said integral vibrator comprises a battery, and said converter system comprises a generator activated by said mechanical energy of flow of fluid in said lumen, and configured to charge said battery.

4. A stent assembly according to claim 1, wherein said integral vibrator comprises a mechanically activated mechanism, and said converter system is a mechanical converter configured to convert the mechanical energy of flow of fluid in said lumen to vibrational energy.

5. A method of reducing restenosis in a bodily lumen to be stented, comprising:
providing a stent assembly comprising:
an outer element comprising a first expandable mesh sheath,
an inner element comprising a second expandable mesh sheath, said inner element having a smaller expanded diameter than that of said outer element, and being disposed axially within said outer element, and in close juxtaposition thereto, and
and integral vibrator mounted on said inner element and adapted to impart vibratory motion to said inner element without involvement external to said luman, said integral vibrator comprising a converter system configured to convert the mechanical energy of flow of fluid in said lumen to vibrational energy; and
inserting said stent assembly into said bodily lumen such that said vibratory motion of said inner element impedes development of stenosis of said bodily lumen.

6. A method according to claim 5, wherein said integral vibrator comprises a battery, and said converter system comprises a generator activated by said mechanical energy of flow of fluid in said lumen, and configured to charge said battery.

7. A method according to claim 5, wherein said integral vibrator comprises a mechanically activated mechanism, and said converter system is a mechanical converter configured to convert the mechanical energy of flow of fluid in said lumen to vibrational energy.

* * * * *